United States Patent [19]

Furutachi et al.

[11] Patent Number: 4,503,141

[45] Date of Patent: Mar. 5, 1985

[54] SILVER HALIDE COLOR PHOTOGRAPHIC LIGHT-SENSITIVE MATERIALS CONTAINING COUPLERS WITH A HYDROXYL SUBSTITUTED AROMATIC HETEROCYCLIC SULFONYL GROUP IN THE BALLAST GROUP

[75] Inventors: Nobuo Furutachi; Takeshi Hirose, both of Kanagawa, Japan

[73] Assignee: Fuji Photo Film Co., Ltd., Kanagawa, Japan

[21] Appl. No.: 592,485

[22] Filed: Mar. 23, 1984

[30] Foreign Application Priority Data

Mar. 28, 1983 [JP] Japan .................................. 58-52924

[51] Int. Cl.$^3$ .......................... G03C 7/26; G03C 7/34
[52] U.S. Cl. ...................................... 430/558; 430/552; 430/553; 430/555; 430/557; 430/565
[58] Field of Search .............. 430/553, 555, 557, 558, 430/565, 552

[56] References Cited

U.S. PATENT DOCUMENTS

| | | | |
|---|---|---|---|
| 2,298,443 | 10/1942 | Weissberger | 430/558 X |
| 2,524,725 | 12/1947 | Coles | 430/558 X |
| 2,524,741 | 12/1947 | Tulagin et al. | 430/558 X |
| 2,589,004 | 3/1952 | Weissberger et al. | 430/470 X |
| 2,908,573 | 10/1959 | Bush et al. | 430/552 |
| 4,201,584 | 5/1980 | Monbaliu et al. | 430/472 X |
| 4,203,768 | 5/1980 | Inouye et al. | 430/470 X |
| 4,289,847 | 9/1981 | Ishikawa et al. | 430/558 X |
| 4,326,024 | 4/1982 | Kobayashi et al. | 430/558 X |
| 4,327,173 | 4/1982 | Aoki et al. | 430/558 X |
| 4,338,393 | 7/1982 | Bailey et al. | 430/558 X |
| 4,443,536 | 4/1984 | Lestinn | 430/558 X |

Primary Examiner—John E. Kittle
Assistant Examiner—Mukund J. Shah
Attorney, Agent, or Firm—Sughrue, Mion, Zinn, Macpeak and Seas

[57] ABSTRACT

A silver halide color photographic light-sensitive material containing at least one coupler having a ballast group represented by the following general formula (I):

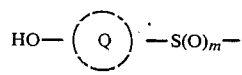

(I)

wherein

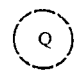

represents a substituted or unsubstituted aromatic heterocyclic ring, and m represents an integer of 1 or 2.

9 Claims, No Drawings

SILVER HALIDE COLOR PHOTOGRAPHIC LIGHT-SENSITIVE MATERIALS CONTAINING COUPLERS WITH A HYDROXYL SUBSTITUTED AROMATIC HETEROCYCLIC SULFONYL GROUP IN THE BALLAST GROUP

FIELD OF THE INVENTION

The present invention relates to color photographic light-sensitive materials containing novel couplers.

BACKGROUND OF THE INVENTION

In order to form color photographic images by a subtractive process, a process of forming cyan, magenta and yellow dye images which comprises reducing silver halide grains in exposed or chemically fogged emulsions with a developing agent such as an aromatic primary amine compound, particularly, a N,N-disubstituted p-phenylenediamine compound to cause reactions of couplers with a simultaneously formed oxidation product of the developing agent is generally utilized.

Couplers used for the above described color developing process are compounds having a phenolic hydroxyl group, an anilinic amino group, an active methylene group or an active methine group which form a dye by oxidative coupling with an aromatic primary amine developing agent.

Suitable couplers which form a cyan dye by reacting with an oxidation product of the color developing agent are phenols and naphthols. Exemplary couplers forming a magenta dye are pyrazolones, pyrazolotriazoles, pyrazolobenzimidazolones, imidazolones, cyanoacetophenones and diaminoaniline, etc. Couplers forming a yellow dye, include -amylacetamides, -ketoacetic acid esters and N,N-malondiamides, etc.

In order to add couplers as described above to photographic emulsion layers, various methods have been proposed. However, it is preferred to use a method of adding couplers which comprises dissolving couplers with a ballast group in the coupler in an organic solvent, and dispersing by the solution emulsification. Characteristics required for such couplers having a ballast group in order to produce color light-sensitive materials having excellent photographic properties are as follows. Namely, (1) Couplers and developed dyes formed by color development have high solubility in high boiling point organic solvents (for example, tricresyl phosphate) used for dispersing the couplers.

(2) Silver halide photographic emulsions having dispersed therein the couplers have high stability and when the emulsions are applied to a support and dried, stable coating films are obtained.

(3) They have an excellent antidiffusion property and do not diffuse into other layers.

(4) They have an excellent dyeing property, and dyed color images have an excellent spectral absorption characteristic. Further, they have good color and density stabilities and high fastness to light.

(5) They can be obtained in good purity and high yield from inexpensive raw materials by a simple synthetic process.

Hitherto, many attempts of modifying the structure of ballast group have been made in order to improve the above described characteristics. Examples of these attempts have been described in Japanese Patent Publication Nos. 5582/67, 5391/71 and 27563/64, U.S. Pat. Nos. 2,589,004 and 2,908,573, Japanese Patent Publication No. 3660/69, U.S. Pat. Nos. 2,474,293, 2,039,970 and 2,920,961, Japanese Patent Publication No. 36078/71, U.S. Pat. No. 2,589,004, British Pat. No. 944,838, Japanese Patent Publication No. 19026/71, U.S. Pat. No. 2,659,329, British Pat. No. 1,813,832, Japanese Patent Application (OPI) No. 76834/78, Japanese Patent Publication No. 36856/79, Japanese Patent Application (OPI) No. 82411/78, German Patent Application (OLS) No. 2,707,488, and Japanese Patent Application (OPI) Nos. 139534/78, 141622/78, 23528/79, 48541/79, 65035/79, 99433/79 and 121126/79, etc.

However, couplers having a ballast group known hitherto have some disadvantages and they do not satisfy the above described characteristics which are required for them. Many of these couplers with an oleophilic ballast group have excellent stability and antidiffusibility in emulsion layers, spectral absorption characteristics of color images, durability of color images and aptitude for synthesis as compared with other types of coupler (for example, couplers having an acid group which are added to emulsion layers as a micellar aqueous solution). However, those which have a satisfactory color forming property have not be found, yet. In rapid processing at high temperature which has been used actively in recent years, the color forming property is particularly important, and insufficient color formation become a serious problem. In order to compensate for this insufficient color formation, depending on the circumstances addition of an organic solvent such as benzyl alcohol as a color forming accelerator to the developing solution has been employed. However, organic solvents for accelerating color formation have some disadvantages. For example, (1) Since they are absorbed in the emulsion layers in the development step, the amount thereof in the developing solution is reduced with deterioration of color formation occurring.

(2) They are carried into the bleaching solution or the blixing solution with obstruction of desilvering or deterioration of dye densities occurring.

(3) They remain in the light-sensitive materials after processing deteriorating the fastness of color images.

(4) They are admixed with waste liquors causing an increase of B.O.D. and C.O.D. in the waste liquors.

Therefore, it has been highly desired to remove or reduce the amount of organic solvents for accelerating color formation.

In couplers containing a ballast group having a p-hydroxyphenylenesulfonyl group of a p-hydroxyphenylenesulfinyl group at the terminal of the group as described in European Patent Publication (Unexamined) No. 73636, improvement of the color forming property is observed as compared with prior couplers, but even so the degree of improvement is not sufficient, yet. Further, they have the disadvantage of having low solubility in organic solvents for dispersing couplers.

SUMMARY OF THE INVENTION

A first object of the present invention is to provide couplers suitable for color photographic light-sensitive materials having excellent photographic properties.

A second object of the present invention is to provide color photographic light-sensitive materials with silver halide emulsions which contain couplers having a novel substituent.

A third object of the present invention is to provide color photographic light-sensitive materials using couplers having a novel substituent by which sufficient color forming property is obtained even if organic solvents for accelerating color formation such as benzyl alcohol, etc. is not present in the color developing solution or is present in reduced amount.

A fourth object of the present invention is to provide color photographic light-sensitive materials suitable for rapid processing at high temperature, wherein novel couplers are used.

As a result of extensive research, it has now been found that the above described objects are attained by providing couplers with a ballast group represented by the following general formula (I):

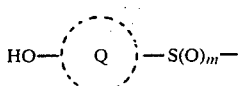
(I)

wherein

represents a substituted or unsubstituted aromatic heterocyclic ring, and m represents an integer of 1 or 2, and silver halide photographic light-sensitive materials containing at least one of these couplers.

DETAILED DESCRIPTION OF THE INVENTION

In the general formula (I), particularly preferred ballast groups are represented by the following general formula (II):

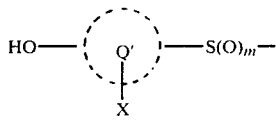
(II)

wherein

represents an unsubstituted aromatic heterocyclic ring containing at least one of an oxygen atom and a sulfur atom, wherein the unsubstituted aromatic heterocyclic ring may be substituted by X.

Specifically, X represents a halogen atom, an alkyl group, an aryl group, a heterocyclic group, a hydroxyl group, an alkoxy group, an aryloxy group, an acylamino group, a sulfonamino group, a carbamoyl group, a sulfamoyl group, a ureido group, an alkoxycarbonyl group, an alkoxycarbonylamino group, a sulfonyl group, an alkylthio group, a cyano group, a nitro group or a carboxyl group and m represents an integer of 1 or 2.

Preferred couplers which can be used in the present invention are represented by the general formula (III):

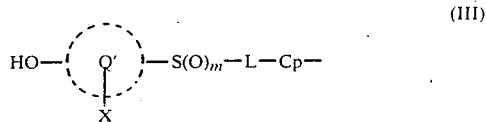
(III)

where Cp represents a coupler residue, L represents a bond or a divalent linking group and X, and m each has the same meaning as in the general formula (I).

Suitable cyan coupler residues for Cp include phenols and naphthols.

Suitable magenta coupler residues for Cp, pyrazolones, pyrazolo[3,2-c]-s-triazoles, pyrazolobenzimidazoles, imidazolones and imidazo[1,2-b]pyrazoles described in Japanese Patent Application No. 23434/83 and pyrazolo[1,5-b]1,2,4-triazoles described in Japanese Patent Application No. 45061/83. Exemplary yellow coupler residues for Cp are α-acylacetamides, β-ketoacetic acid esters, β-diketones and N,N-malondiamides, etc.

Further, in addition to them, coupler residues for Cp forming a black or gray dye by reacting with an oxidation product of the color developing agent include resorcinols and 3-aminophenols, etc. Further, coupler residues for Cp forming a coloring compound by reaction with an oxidation product of the color developing agent, are indanes and acetophenones, etc.

In the above general formula (II), the coupler residue represented by Cp may have sustituents other than a hydrogen atom at the positions where a coupling reaction with an oxidation product of the color developing agent (coupling positions) occurs.

In greater detail, X represents a halogen atom, an alkyl group (for example, an unsubstituted or substituted alkyl group such as a methyl group, a trifluoromethyl group, a t-butyl group, an isopropyl group, a t-octyl group or a 2-ethoxyethyl group, etc.), an aryl group (for example, an unsubstituted or substituted aryl group such as a phenyl group, a 2-chlorophenyl group or a 4-cyanophenyl group, etc.), a heterocyclic group (for example, a 2-furyl group, a 2-benzothiazolyl group, a 2-pyridyl group or a 2-oxazolyl group, etc.), a hydroxyl group, an alkoxy group (for example, an unsubstituted or substituted alkoxy group such as a methoxy grop, a propyloxy group, an isobutyloxy group, or a dodecyloxy group, etc.), an aryloxy group (for example, an unsubstituted substituted aryloxy group such as a phenoxy group, a 4-chlorophenoxy group or a 2-naphthyloxy group, etc.), an acylamino group (for example, an acetamido group, a benzamide group, a hexanoic amido group, a 3-chlorobenzamido group or an α-(2,4-di-t-amylphenoxy)acetamido group, etc.), a sulfonamido group (for example, a methanesulfonamido group, a butanesulfonamido group, a benzenesulfonamido group, a 4-toluenesulfonamido group or a dodecanesulfonamido group, etc.), a carbamoyl group (for example, a N-butylcarbamoyl group, a N,N-diethylcarbamoyl group, a N-acetyl-N-octylcarbamoyl grop or a 3-phenoxypropylcarbamoyl group, etc.), a sulfamoyl group (for example, a N-butylsulfamoyl group, a N,N-dipropylsulfamoyl group or a N-octadecylsulfamoyl group, etc.), a ureido group (for example, a phenylureido group, an ethylureido group, a p-cyanophenylureido group or a dodecylureido group, etc.), an alkoxycarbonyl group (for example, a methoxycarbonyl group, an ethoxycarbonyl group or a dodecyloxycarbonyl group, etc.), an alkoxycarbonylamino group (for example, a methoxycarbonylamino group, an ethoxycarbonylamino group or a dodecyloxycarbonylamino group, etc.), a sulfonyl group (for example, a methanesulfonyl group, a propanesulfonyl group, a benzenesulfonyl group, a 4-cyanobenzenesulfonyl group or a hexadecanesulfonyl group, etc.), an alkylthio group (for example, an ethylthio group, an octylthio group or a tetradecylthio group, etc.), a cyano group, a nitro group or a carboxy group; and L represents

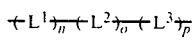

wherein n, o and p represent each 0 or 1, $L^1$ represents a divalent group selected from groups of the formula

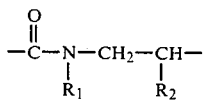

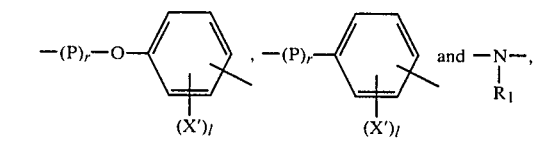

$L^2$ represents a divalent group selected from groups of the formula

and $L^3$ represents a divalent group selected from groups of the formula wherein $R_1$ and $R_2$ represent each a hydrogen atom, an alkyl group having 1 to 20 carbon atoms or an aryl group having 6 to 20 carbon atoms; X' represents the same meaning as described above in X or a hydrogen atom; Y represents —O— or —S—; P represents or —SO₂—; r represents 0 or 1; s represents an integer of 0 to 10 and l represents an integer of 1 to 4. In greater detail, Cp represents

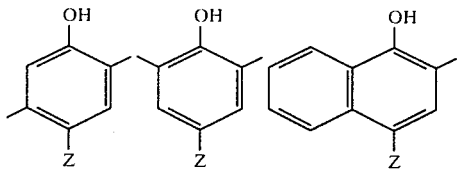

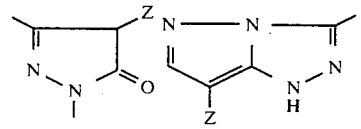

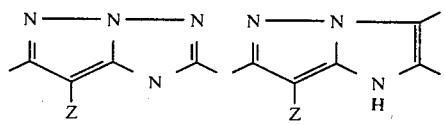

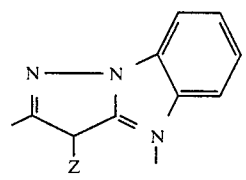

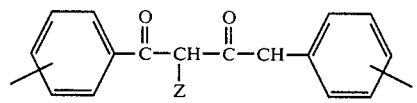

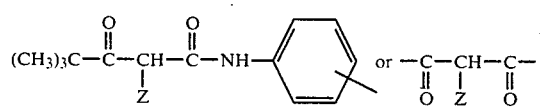

As a nucleus which does not form a dye, Cp represents

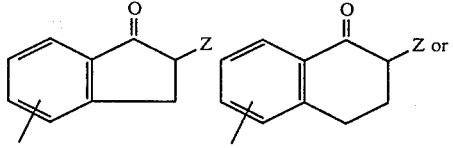

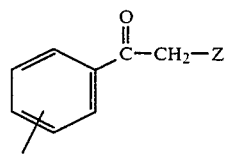

As a nucleus which forms a black or brown dye, Cp represents

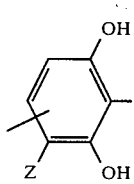

In the above formulae, Z represents a hydrogen atom or an atom or group which is released by coupling. Examples of preferred groups which are released by coupling include halogen atoms and groups linked to the nucleus Cp through an oxygen atom, a nitrogen atom or a sulfur atom. In greater detail, groups will become obvious from examples of the couplers shown below.

On the other hand, as preferred

Q′, there are following nuclei.

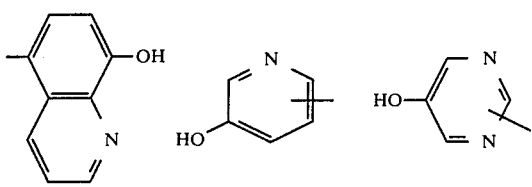

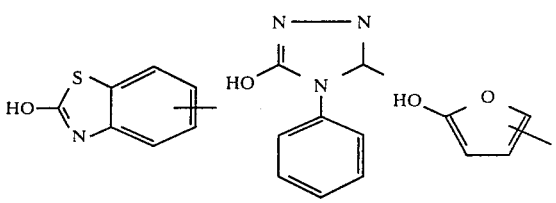

Couplers according to the present invention are described below, but the present invention is not to be construed as being limited to these couplers.

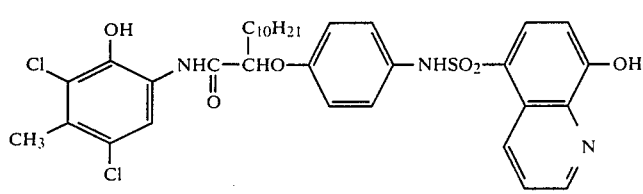

C-1

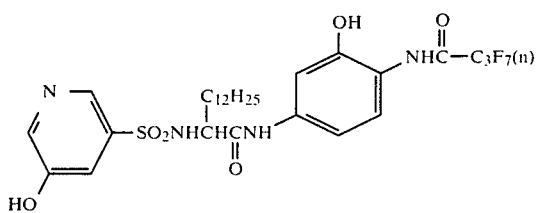

C-2

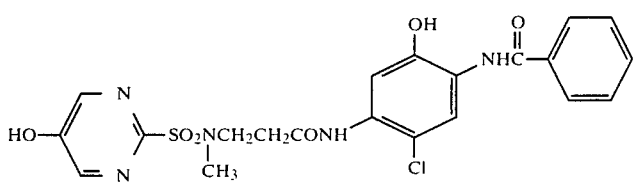

C-3

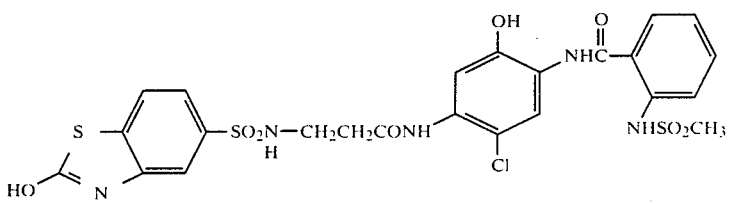

C-4

-continued
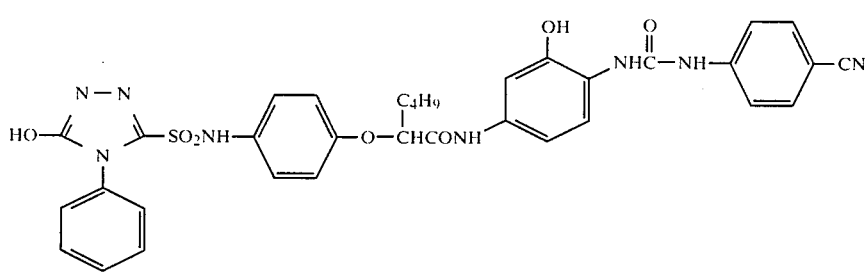
C-5
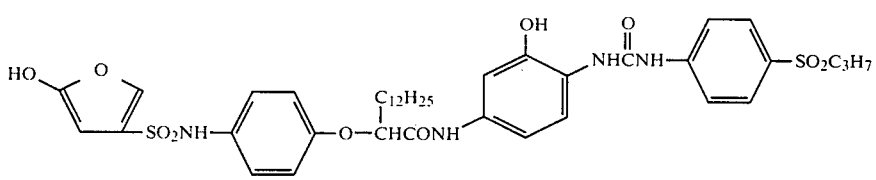
C-6
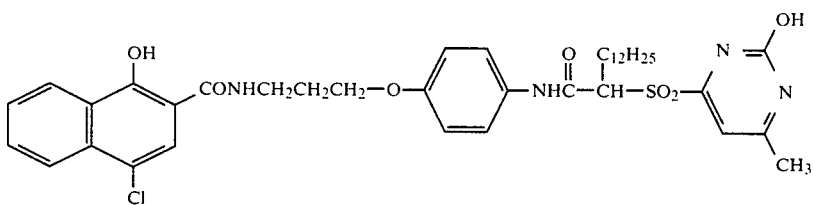
C-7
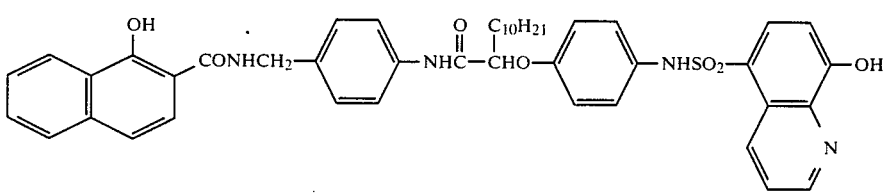
C-8
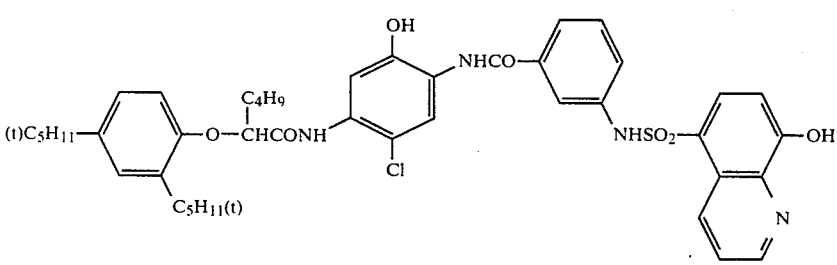
C-9
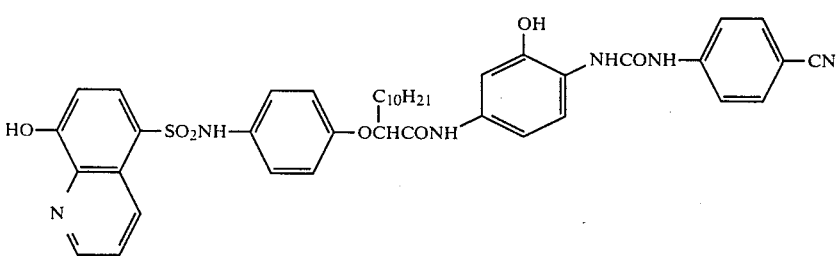
C-10

-continued
M-1
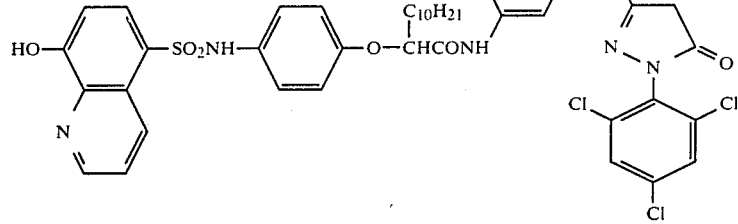
M-2
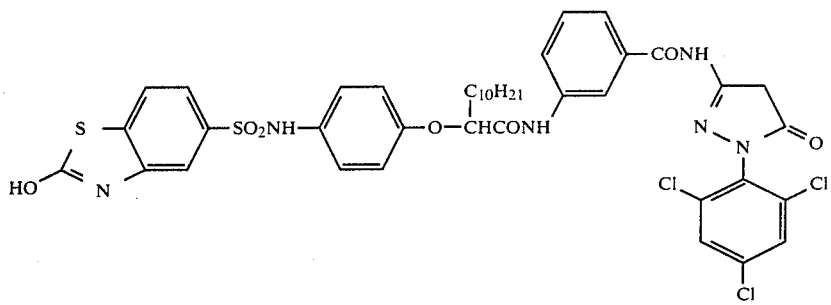
M-3
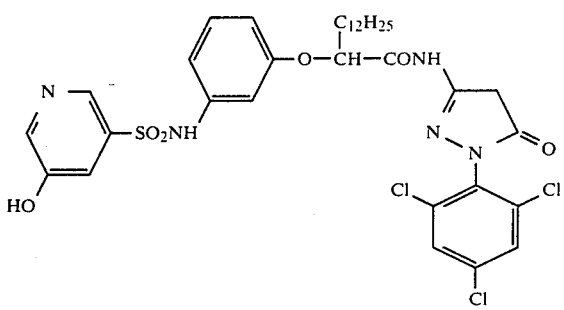
M-4
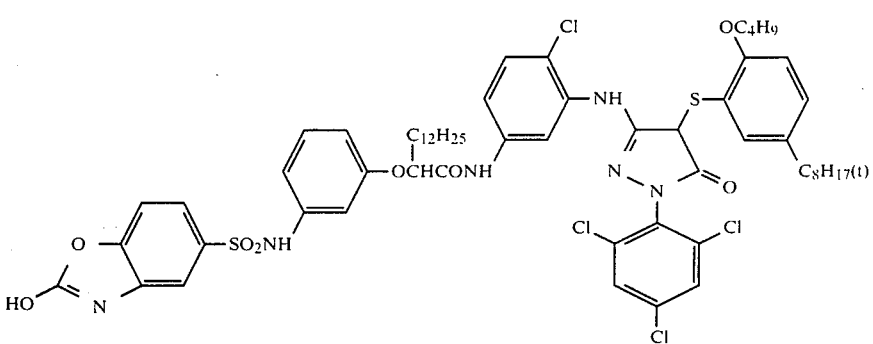
M-5
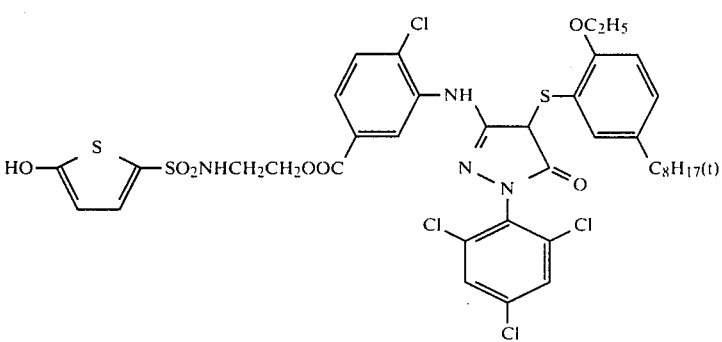

-continued
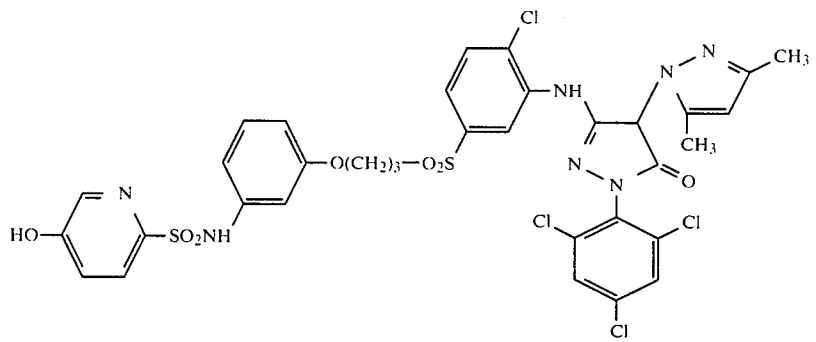
M-6
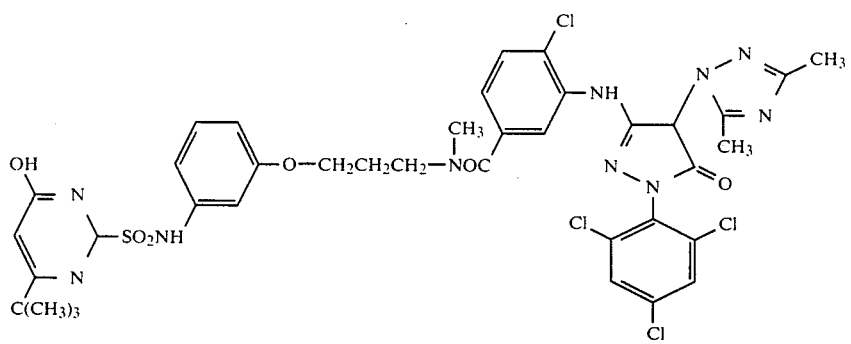
M-7
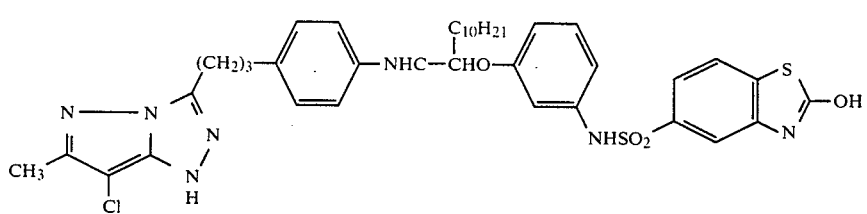
M-8
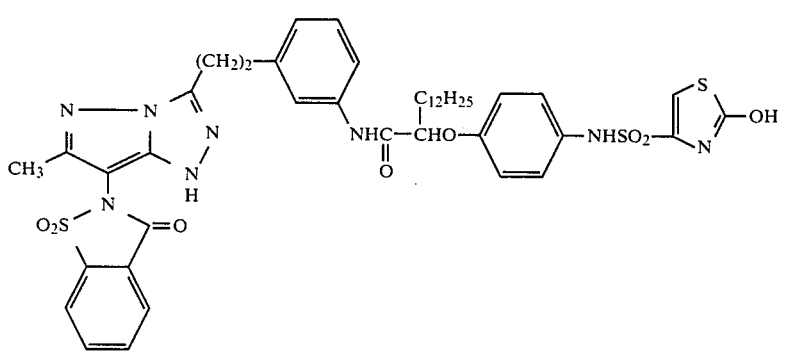
M-9

-continued
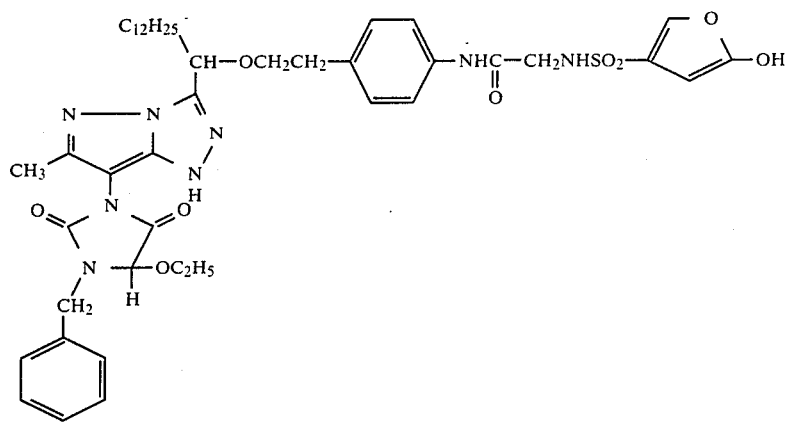 M-10
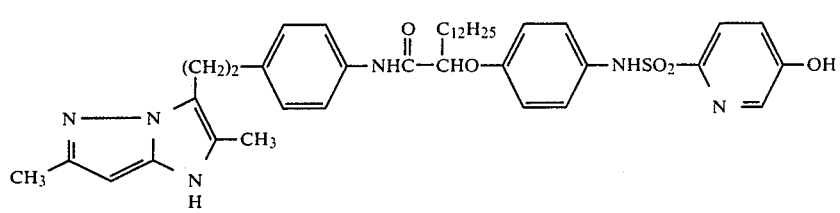 M-11
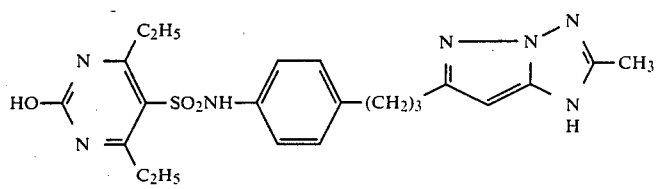 M-12
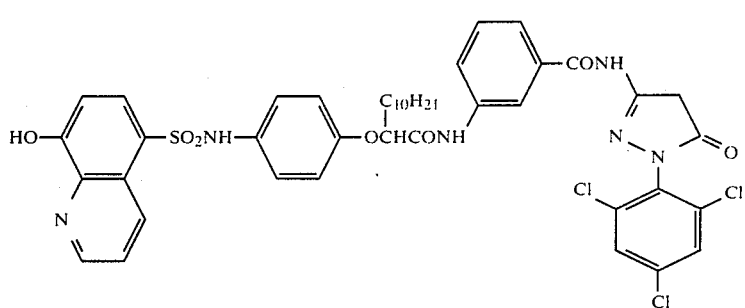 M-13
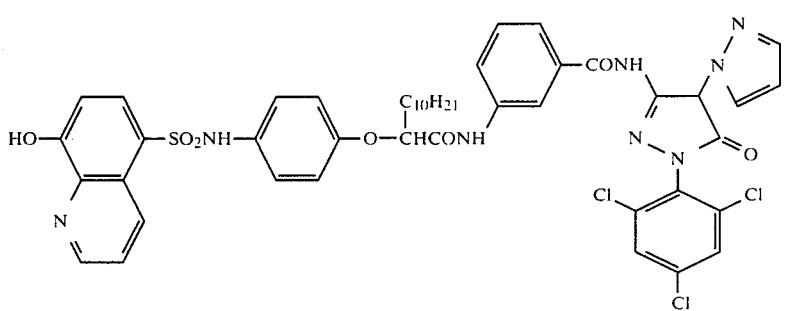 M-14

-continued
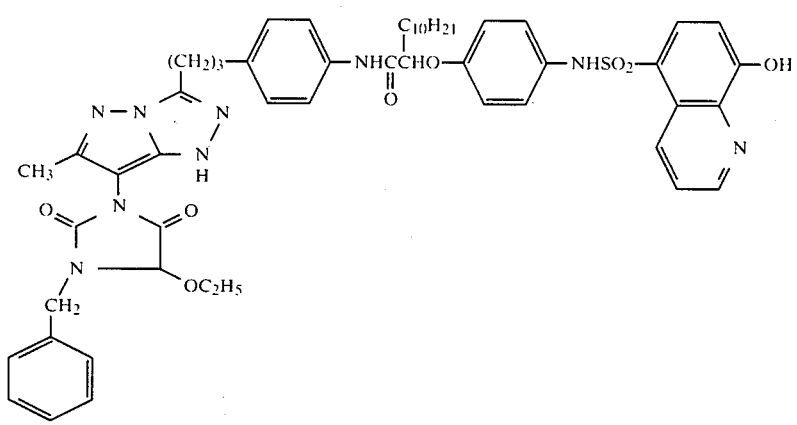
M-15
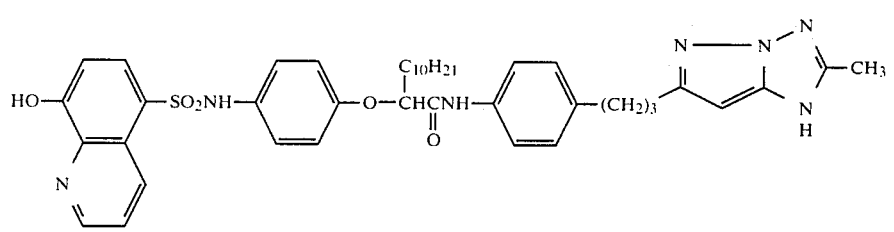
M-16
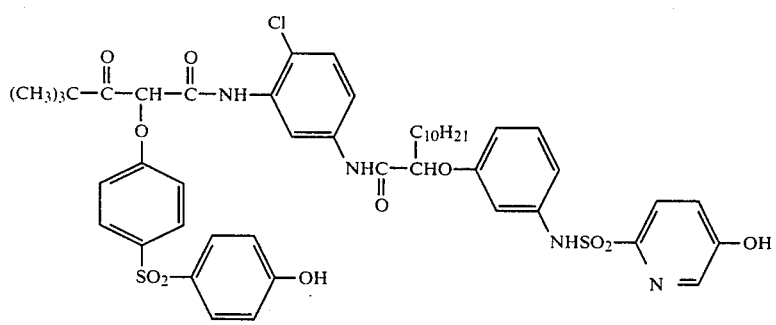
Y-1
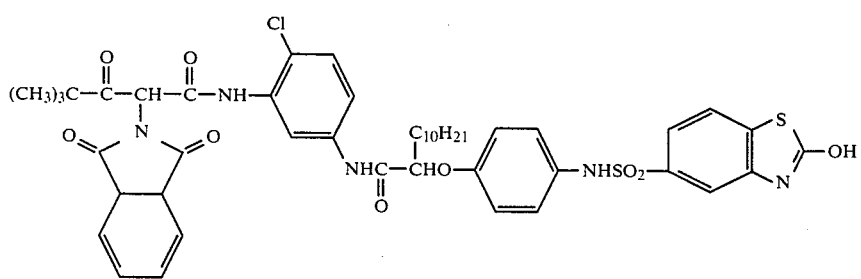
Y-2
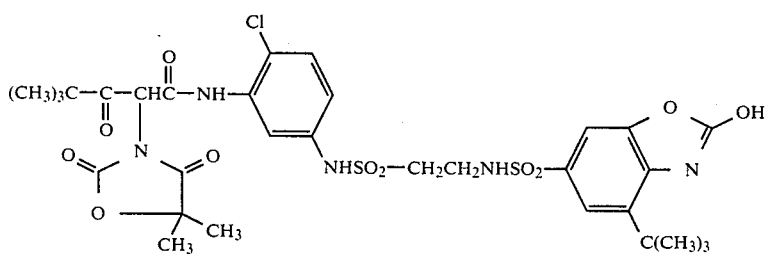
Y-3

-continued
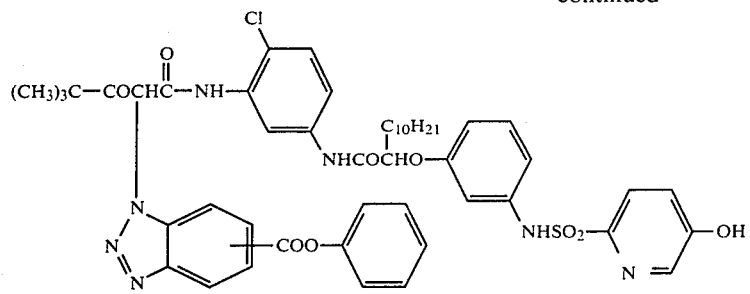
Y-4
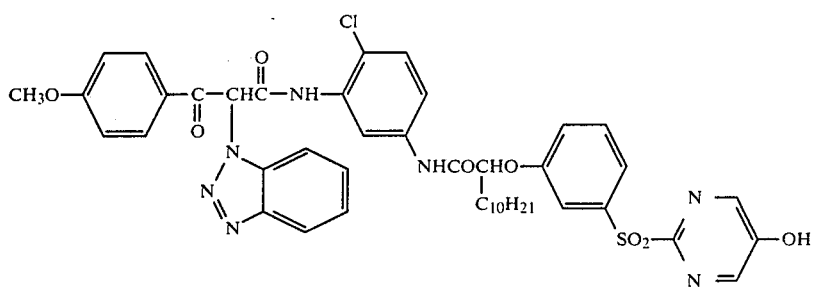
Y-5
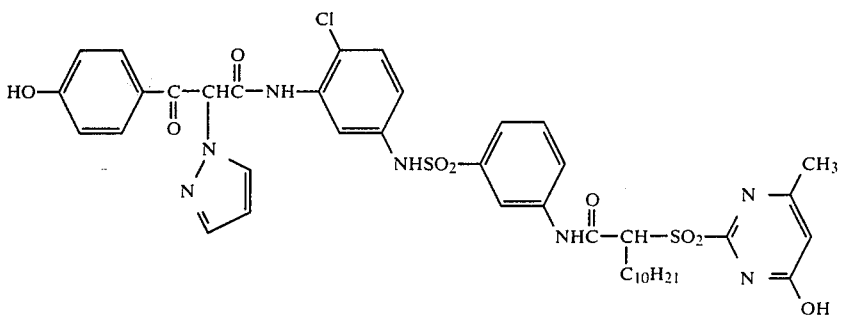
Y-6
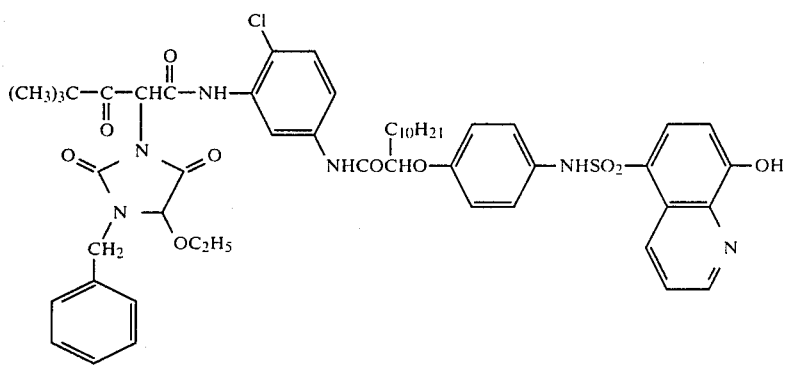
Y-7
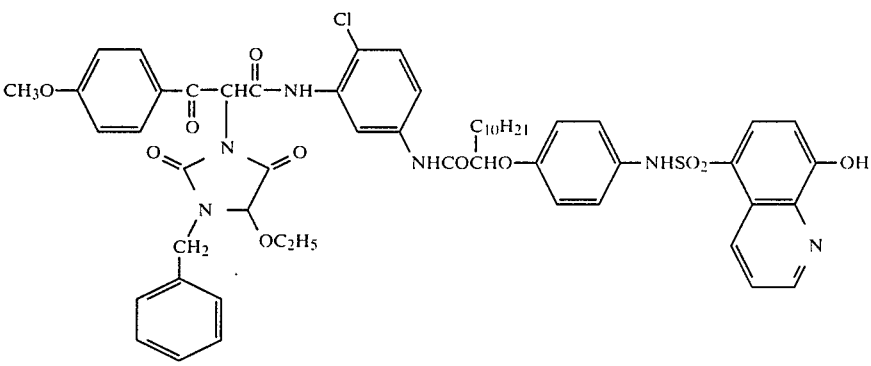
Y-8

Couplers with a hydroxyl substituted aromatic heterocyclic sulfonyl group in the ballast group according to the present invention can be synthesized by reacting an aromatic amine compound with a heterocyclic sulfonyl chloride. The hydroxyl substituted aromatic heterocyclic sulfonyl group can be obtained by sulfonating a heterocyclic ring with a hydroxyl group which is commercially available using the process described in *Organic Functional Group Preparation*, Vol. 1, Chapter 21, Academic Press (1968), protecting the hydroxyl group with a suitable protective group (for example, a benzyl group or an acetyl group, etc.) and converting the product into a sulfonyl chloride with thionyl chloride or phosphorus oxychloride, or converting the product directly into sulfonyl chloride depending on the heterocyclic ring with out protecting the hydroxyl group with a protective group, and carrying out sulfonamidation.

The following synthesis examples are given to illustrate the synthesis of couplers used in the present invention. Unless otherwise indicated all parts, percents, ratios and the like are by weight.

SYNTHESIS EXAMPLE 1

Synthesis of Coupler C-1

4,6-Dichloro-5-methyl-2-[2-(4-aminophenoxy)-dodecanamido]phenol was dissolved in pyridine. On the other hand, 8-hydroxyquinoline-5-sulfonic acid was added to phosphorus oxychloride. The mixture was refluxed with heating and excess phosphorus oxychloride was removed under reduced pressure. The solidified sulfonyl chloride intermediate was added to an equimolar amount of the above described pyridine solution under a nitrogen stream, and the resulting mixture was stirred at room temperature (about 20° to 30° C.). After conclusion of the reaction, the mixture was poured into ice water and the crystals separated were collected by filtration. After drying the crystals well, crystals were crystallized from a mixture of acetonitrile-ethyl acetate (50:50 by vol) to obtain the desired coupler C-1.

SYNTHESIS EXAMPLE 2

Synthesis of Coupler M-1

1-(2,4,6-Trichlorophenyl)-3-{2-chloro-5-[2-(4-aminophenoxy)dodecanamido]anilino}-5-oxo-2-pyrazoline was synthesized by the well known process similar to the description in Synthesis Example 1. The compound was dissolved in pyridine, and the sulfonyl chloride intermediate obtained as described in Synthesis Example 1 was added in an equimolar amount thereto and stirred under nitrogen. After conclusion of the reaction, the mixture was poured into ice water, and the separated solid was collected by filtration and dried well. The product was purified by silica gel chromatography to obtain the desired Coupler M-1.

The amount of the couplers which can be used in the present invention is not restricted, but it is preferred to be in a range of $2 \times 10^{-3}$ mols to $5 \times 10^{-1}$ mols, preferably $1 \times 10^{-2}$ mols to $5 \times 10^{-1}$ mols, per mol of silver in the silver halide emulsion layer.

In order to introduce couplers into silver halide emulsion layers, known processes, for example, a process described in U.S. Pat. No. 2,322,027, etc. can be used. For example, after the couplers are dissolved in phthalic acid alkyl esters (dibutyl phthalate and dioctyl phthalate, etc.), phosphoric acid esters (diphenyl phosphate, triphenyl phosphate, tricresyl phosphate and dioctylbutyl phophate), citric acid esters (for example, tributyl acetylcitrate), benzoic acid esters (for example, octyl benzoate), alkylamides (for example, diethyllaurylamide), aliphatic acid esters (for example, dibutoxyethyl succinate) or trimesic acid esters, or organic solvents having a boiling point of about 30° to 150° C., for example, lower alkyl acetates such as ethyl acetate or butyl acetate, ethyl propionate, secondary butyl alcohol, methyl isobutyl ketone, β-ethoxyethyl acetate and methyl cellosolve acetate, etc., they were dispersed in hydrophilic colloids. The above described high boiling point organic solvents and the low boiling point organic solvents may be used alone or as a mixture thereof, if desired.

The following examples are given to further illustrate the present invention. Again, all parts, percents, ratios and the like are by weight unless otherwise indicated.

EXAMPLE 1

10 g of a Coupler C-1 of the present invention was dissolved in a mixture of 5 ml of dibutyl phthalate and 10 ml of ethyl acetate, and the resulting solution was blended with 100 ml of a 10% aqueous solution of gelatin containing 0.1 g of sodium dodecylbenzenesulfonate and was stirred at 50° C. using a homogenizer revolving at a high rate to obtain a coupler emulsified dispersion. This dispersion was blended with 178 g of a silver chlorobromide emulsion (Cl/Br: 30/70 by mol; silver: 70 g/kg emulsion), and 15 ml of a 2% aqueous solution of 2-hydroxy-4,6-dichloro-s-triazine Na salt and 6 ml of a 5% aqueous solution of saponin were added thereto. The mixture was applied to a cellulose acetate film so as to result in a silver coating amount of 1 g/m² and a gelatin protective layer having a dry film thickness of 1μ was applied to the resulting layer to produce Sample A. Samples B-L were produced in the same manner as for Sample A as shown in Table 1 below, except that the molar amount of the coupler applied and the amount of silver applied were adjusted so as to be equal to those in Sample A.

After Samples A-R were exposed stepwise to light for sensitometry, the exposed samples were subjected to the following development processing.

| Process | Temperature | Time |
|---|---|---|
| Color Development | 38° C. | 3 minutes |
| Water Wash | " | 1 minute |
| Blixing | " | 1 minute and 30 seconds |
| Water Wash | " | 1 minute |

The composition of the color developing solutions used was as follows.

| | CD - 1 | CD - 2 | CD - 3 |
|---|---|---|---|
| Benzyl Alcohol | — | — | 15 ml |
| Diethylene Glycol | — | — | 8 ml |
| Developing Agent | 4-Amino-3-methyl-N—ethyl-N—β-hydroxyethyl-aniline sulfate | 4-Amino-3-methyl-N—ethyl-N—β-(methanesulfon-amido)ethylaniline sulfate | Same as CD - 2 |
| | 3.5 g | 5 g | 5 g |
| Sodium Sulfite | 2 g | 2 g | 2 g |
| Hydroxyl-amine Sulfate | 3 g | 3 g | 3 g |
| Potassium Carbonate | 30 g | 30 g | 30 g |

-continued

|  | CD-1 | CD-2 | CD-3 |
|---|---|---|---|
| Water to make | 1 l | 1 l | 1 l |
| pH (adjusted) | 10.2 | 10.2 | 10.2 |

The composition of the blixing solution was as follows.

| Disodium Ethylenediaminetetraacetate | 2 g |
|---|---|
| Ethylenediamine Tetraacetic Acid Ferric Salt | 40 g |
| Sodium Sulfite | 5 g |
| Ammonium Thiosulfate | 70 g |
| Water to make | 1 l |
| pH was adjusted to 6.8 | |

The transmitted light densities of each resulting sample were measured (cyan, magenta or yellow density was measured according to each dye) and the maximum densities and γ were determined. The results obtained are shown in Table 1 below.

TABLE 1

| | | CD-1 | | CD-2 | | CD-3 | |
|---|---|---|---|---|---|---|---|
| Sample | Coupler | Dmax | γ | Dmax | γ | Dmax | γ |
| A | C-1 | 3.25 | 2.31 | 3.20 | 2.27 | 3.30 | 2.41 |
| B | C-8 | 3.21 | 2.30 | 3.19 | 2.27 | 3.29 | 2.31 |
| C | CR-1 | 2.80 | 1.88 | 2.23 | 1.43 | 2.78 | 1.90 |
| D | CR-2 | 2.65 | 1.52 | 2.01 | 1.22 | 2.72 | 1.58 |
| E | M-1 | 3.47 | 2.51 | 3.29 | 2.48 | 3.32 | 2.46 |
| F | M-13 | 3.52 | 2.57 | 3.44 | 2.51 | 3.61 | 2.61 |
| G | MR-1 | 2.93 | 2.02 | 2.77 | 1.92 | 3.16 | 2.11 |
| H | MR-2 | 3.03 | 2.08 | 2.87 | 1.94 | 3.08 | 2.10 |
| I | Y-3 | 3.21 | 2.25 | 3.20 | 2.21 | 3.28 | 2.39 |
| J | Y-7 | 3.32 | 2.44 | 3.30 | 2.40 | 3.38 | 2.43 |
| K | YR-1 | 3.00 | 1.98 | 2.64 | 1.57 | 2.98 | 1.95 |
| L | YR-2 | 2.81 | 1.43 | 2.15 | 1.21 | 2.79 | 1.55 |

The comparative couplers used for comparison are shown below.

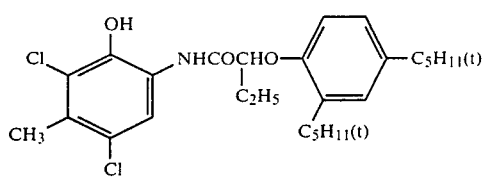

CR-1

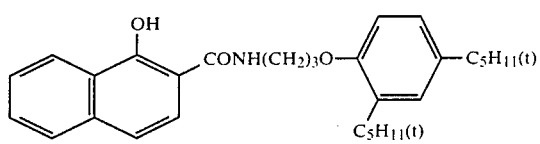

CR-2

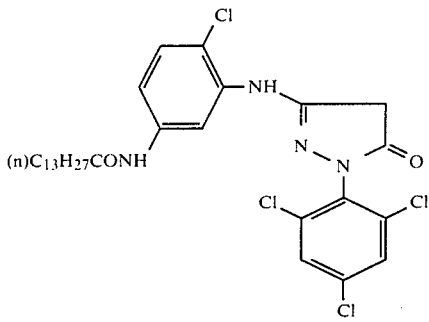

MR-1

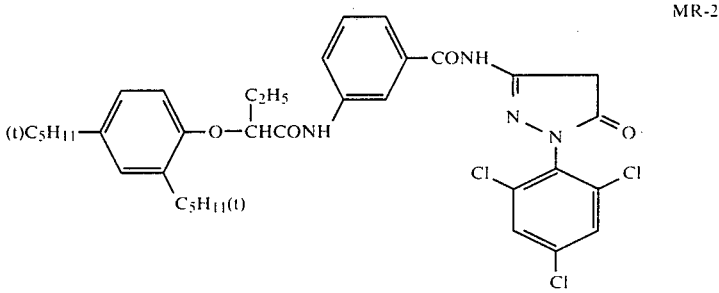

MR-2

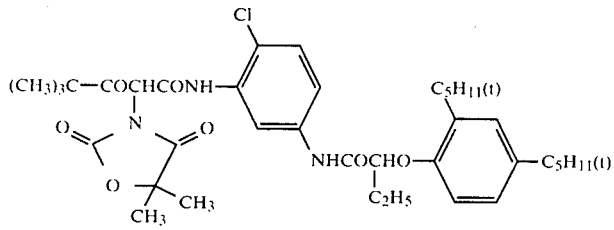

YR-1

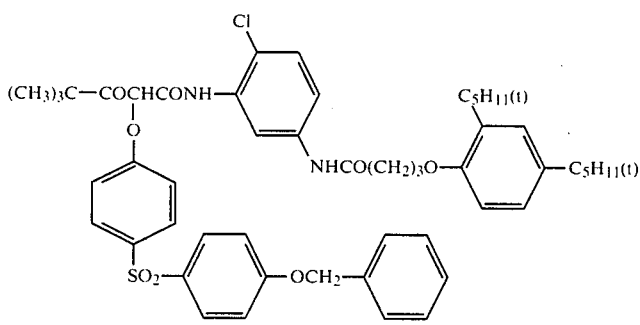

YR-2

It can be seen from these results that good color formation is achieved in the Samples containing couplers of the present invention, even if processed with any color developing solution, while Dmax or γ is low and color formation is poor in the Comparative Samples. Particularly, it can be seen from a comparison of CD-2 and CD-3, which contain the same comparatively active color developing agent, that the Comparative Samples undergo serious deterioration of color formation when processed with CD-2 which does not contain benzyl alcohol, while the Samples of the present invention exhibit only a small difference between the case of using CD-2 and the case of using CD-3 and sufficient color formation can be achieved without using benzyl alcohol.

EXAMPLE 2

To a laminated paper, both sides of which were covered with polyethylene, a first layer (the lowest layer)—a sixth layer (the top layer) were applied as shown in Table 2 below to produce color photographic light-sensitive materials, Samples A and B.

The coating solution for the first layer was prepared as follows. 10 g of the yellow coupler shown in Table 2 was dissolved in a mixture of 166.7 ml of dibutyl phthalate (DBP) and 200 ml of ethyl acetate, and the resulting solution was dispersed by emulsification in 800 g of a 10% aqueous solution of gelatin containing 80 ml of a 1% aqueous solution of sodium dodecylbenzene sulfonate, and the resulting emulsified dispersion was then blended with 1450 g (containing 66.7 g of Ag) of a blue-sensitive silver chlorobromide emulsion (Br: 80 mol%) to prepare a coating solution. Coating solutions for the other layers were prepared in the same manner as described above. 2,4-Dichloro-6-hydroxy-s-triazine sodium salt was used as a hardening agent for each layer.

Further, the following compounds were used as spectral sensitizers for each emulsion.

Blue-Sensitive Emulsion Layer: 3,3'-Di-(γ-sulfopropyl)selenocyanine sodium salt ($2 \times 10^{-4}$ mols per mol of silver halide)

Green-Sensitive Emulsion Layer: 3,3'-Di-(γ-sulfopropyl)-5,5'-diphenyl-9-ethyloxacarbocyanine sodium salt ($2.5 \times 10^{-4}$ mols per mol of silver halide)

Red-Sensitive Emulsion Layer: 3,3'-Di-(γ-sulfopropyl)-9-methyl-thiadicarbocyanine sodium salt ($2.5 \times 10^{-4}$ mols per mol of silver halide).

The following dyes were used as anti-irradiation dyes in each emulsion layer.

GREEN-SENSITIVE EMULSION LAYER

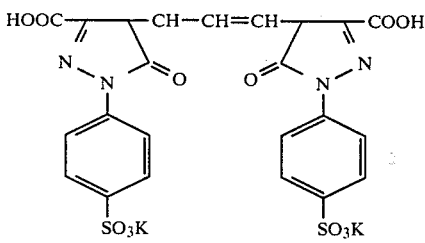

RED-SENSITIVE EMULSION LAYER

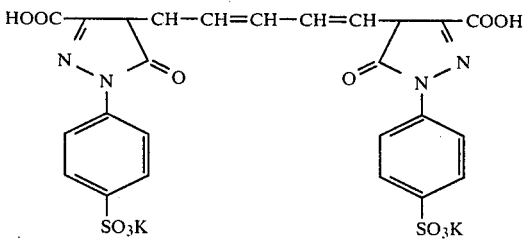

The Chemical Structures of the Solvents in Table 2 are as follows.

TABLE 2

DBP:

$$\begin{array}{c}\text{COOC}_4\text{H}_9\\\text{C}_6\text{H}_4\\\text{COOC}_4\text{H}_p\end{array}$$

TOP: 
$$\begin{array}{c}\text{C}_8\text{H}_{17}-\text{O}\\|\\\text{C}_8\text{H}_{17}\text{O}-\text{P}=\text{O}\\|\\\text{C}_8\text{H}_{17}-\text{O}\end{array}$$

| | | Sample No. A | Sample No. B |
|---|---|---|---|
| Sixth Layer: (protective layer) | Amount of Gelatin Applied | 1500 mg/m² | 1500 mg/m² |
| Fifth Layer: (red-sensitive layer) | Silver Chlorobromide Emulsion (Br: 50 mol %) | | |
| | Amount of Ag | 300 mg/m² | 300 mg/m² |
| | Cyan Coupler | CR - 1 | C - 1 |
| | Amount applied | 400 mg/m² | 560 mg/m² |
| | Solvent | DBP | DBP |
| | Amount of solvent applied | 240 mg/m² | 330 mg/m² |
| Fourth Layer: (ultraviolet ray absorbing layer) | Amount of Gelatin Applied | 2000 mg/m² | 2000 mg/m² |
| | Ultraviolet Ray Absorbing Agent Amount applied | UV-1: 15 mg/m² UV-2: 45 mg/m² UV-3: 90 mg/m² | UV-1: 15 mg/m² UV-2: 45 mg/m² UV-3: 90 mg/m² |
| | Solvent | DBP | DBP |
| | Amount of solvent applied | 60 mg/m² | 60 mg/m² |
| Third Layer: (green-sensitive layer) | Silver Chlorobromide Emulsion (Br: 70 mol %) | | |
| | Amount of Ag | 450 mg/m² | 450 mg/m² |
| | Magenta Coupler | MR - 1 | M - 1 |
| | Amount applied | 350 mg/m² | 505 mg/m² |
| | Solvent | TOP | TOP |
| | Amount of solvent applied | 440 mg/m² | 620 mg/m² |
| Second Layer: (intermediate layer) | Amount of Gelatin Applied | 1500 mg/m² | 1500 mg/m² |
| First Layer: (blue-sensitive layer) | Silver Chlorobromide Emulsion (Br: 80 mol %) | | |
| | Amount of Ag | 1500 mg/m² | 1500 mg/m² |
| | Yellow Coupler | YR - 1 | Y - 7 |
| | Amount applied | 600 mg/m² | 860 mg/m² |
| | Solvent | DBP | DBP |
| | Amount of solvent applied | 1000 mg/m² | 1120 mg/m² |
| Support | Laminated paper support, both sides of which were covered with polyethylene | | |

After each sample was exposed stepwise to light for sensitometry, development processing was carried out in the same manner as described in Example 1. However, as color developing solutions, CD-2 and CD-3 were used. The reflection densities (red, green and blue densities) of the resulting processed samples were measured, and fog, Dmax and $\gamma$ were determined. The results obtained are shown in Table 3 below.

which does not contain benzyl alcohol: CD-2, while Samples B and C of the present invention exhibits excellent color formation even if CD-2 is used.

UV-1, UV-2 and UV-3 in Table 2 above are compounds having the following structure.

TABLE 3

| | CD - 2 | | | | | | | | |
|---|---|---|---|---|---|---|---|---|---|
| | Cyan | | | Magenta | | | Yellow | | |
| Sample | Fog | $\gamma$ | Dmax | Fog | $\gamma$ | Dmax | Fog | $\gamma$ | Dmax |
| A | 0.08 | 2.78 | 2.12 | 0.07 | 2.82 | 2.23 | 0.09 | 2.84 | 2.14 |
| B | 0.11 | 3.30 | 2.68 | 0.09 | 3.35 | 2.75 | 0.12 | 3.13 | 2.74 |

| | CD - 3 | | | | | | | | |
|---|---|---|---|---|---|---|---|---|---|
| | Cyan | | | Magenta | | | Yellow | | |
| Sample | Fog | $\gamma$ | Dmax | Fog | $\gamma$ | Dmax | Fog | $\gamma$ | Dmax |
| A | 0.10 | 3.23 | 2.58 | 0.08 | 3.39 | 2.72 | 0.12 | 3.10 | 2.69 |
| B | 0.12 | 3.48 | 2.80 | 0.12 | 3.42 | 2.81 | 0.14 | 3.33 | 2.94 |

It can be seen from these results that Comparative Sample A undergoes serious deterioration of $\gamma$ and Dmax in case of using the color developing solution

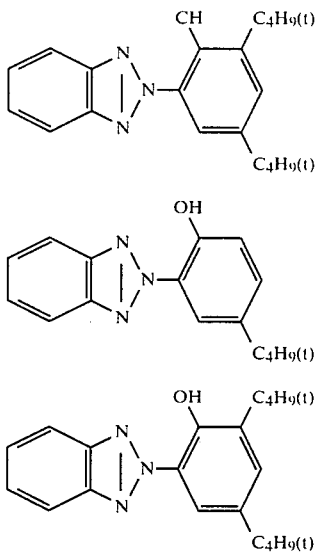

UV-1
UV-2
UV-3

Couplers other than those of the present invention and constructions of the color light-sensitive materials which can be used in the present invention are described below.

Known ring-opened ketomethylene type couplers can be used as yellow couplers. Among others, benzoylacetanilide type compounds and pivaloylacetanilide type compounds can be advantageously used. Examples of yellow couplers capable of being used include those described in U.S. Pat. Nos. 2,875,057, 3,265,506, 3,408,194, 3,551,155, 3,582,322, 3,725,072 and 3,891,445, German Pat. No. 1,547,868, German Patent Application (OLS) Nos. 2,219,917, 2,261,361 and 2,414,006, British Pat. No. 1,425,020, Japanese Patent Publication No. 10783/76 and Japanese Patent Application (OPI) Nos. 26133/72, 73147/73, 102636/76, 6341/75, 123342/75, 130442/75, 21826/76, 87650/75, 82424/77 and 115219/77, etc.

Pyrazolone type compounds, imidazolone type compounds and cyanoacetyl type compounds, etc. can be used as magenta couplers. Particularly, pyrazolone type compounds can be advantageously used. Examples of magenta couplers capable of being used include those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Pat. No. 1,810,464, German Patent Application (OLS) Nos. 2,408,665, 2,417,945, 2,418,959 and 2,424,467, Japanese Patent Publication No. 6031/65 and Japanese Patent Application (OPI) Nos. 20826/76, 58922/77, 129538/74, 74027/74, 159336/75, 42121/77, 74028/74, 60233/75, 26541/76 and 55122/78, etc.

Phenol type compounds and naphthol type compounds, etc. can be used as cyan couplers. Examples of these couplers include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Application (OLS) Nos. 2,414,830 and 2,454,329 and Japanese Patent Application (OPI) Nos. 59838/73, 26034/76, 5055/73, 146828/76, 69624/77 and 90932/77.

It is possible to use, for example, those described in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, and German Patent Application (OLS) No. 2,418,959 as colored couplers.

It is possible to use, for example, those described in U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454, Japanese Patent Application (OPI) Nos. 69624/77 and 122335/74 and Japanese Patent Publication No. 15141/76 as development inhibitor releasing (DIR) couplers.

The light-sensitive materials used in the present invention may contain compounds which release a development inhibitor on development, other than DIR couplers. For example, it is possible to use those described in U.S. Pat. Nos. 3,297,445 and 3,379,529, German Patent Application (OLS) No. 2,417,914 and Japanese Patent Application (OPI) Nos. 15271/77 and 9116/78.

Two or more of the above described couplers may be present in the same layer if desired. The same compound also may be present in two or more different layers if desired. These couplers are generally employed in an amount of $2 \times 10^{-3}$ mols to $5 \times 10^{-1}$ mols, preferably, $1 \times 10^{-2}$ mols to $5 \times 10^{-1}$ mols, per mol of silver in the emulsion layer.

Hydrophilic colloid layers used in the light-sensitive materials produced according to the present invention may contain ultraviolet ray absorbing agents. For example, it is possible to use benzotriazole compounds substituted with aryl groups (for example, those described in U.S. Pat. No. 3,533,794), 4-thiazolidone compounds (for example, those described in U.S. Pat. Nos. 3,314,794 and 3,352,681), benzophenone compounds (for example, those described in Japanese Patent Application (OPI) No. 2784/71), cinnamic acid ester compounds (for example, those described in U.S. Pat. Nos. 3,705,805 and 3,707,375), butadiene compounds (for example, U.S. Pat. No. 4,045,229) and benzoxazole compounds. Further, compounds described in U.S. Pat. No. 3,499,762 and Japanese Patent Application (OPI) No. 48535/79 can be employed. Ultraviolet ray absorbing couplers (for example, α-naphthol type cyan dye forming couplers) or ultraviolet ray absorbing polymers, etc. may be used, too. These ultraviolet ray absorbing agents may be mordanted in a specified layer, if desired.

The photographic emulsions used in the present invention can be prepared according to processes described in P. Glafkides, *Chimie et Physique Photographique* (published by Paul Montel Co., 1977), G. F. Duffin, *Photographic Emulsion Chemistry* (published by The Focal Press, 1966) and V. L. Zelikman et al, *Making and Coating Photographic Emulsion* (published by The Focal Press, 1964), etc. Namely, any of acid processes, neutral processes and ammonia processes may be used. Further, as the type of reaction of soluble silver salts with soluble halogen salts, any of one-side mixing processes, simultaneous mixing processes and combinations thereof may be used.

It is also possible to use a process wherein grains are formed in a presence of excess silver ions (the so-called back-mixing process). As a type of the simultaneous mixing process, it is possible to use a process wherein the liquid phase of forming silver halide is kept at a constant pAg, namely, the so-called controlled double jet process, too. According to this process, silver halide emulsions having a regular crystal form and a nearly uniform particle size are obtained.

Two or more silver halide emulsions produced respectively may be used as a mixture, if desired.

Formation of silver halide grains or physical ageing may be carried out in a presence of cadmium salts, zinc salts, lead salts, thallium salts, iridium salts or complex salts thereof, rhodium salts or complex salts thereof, and iron salts or complex salts thereof, etc.

Gelatin is advantageously used as binders or protective colloids for photographic emulsions, but other hydrophilic colloids can be used, too.

For example, it is possible to use proteins such as gelatin derivatives, graft polymers of gelatin and other high polymers, albumin or casein, etc., saccharose derivatives such as cellulose derivatives such as hydroxyethyl cellulose, carboxymethyl cellulose or cellulose sulfate, etc., sodium alginate or starch derivatives, etc., and synthetic hydrophilic high molecular weight substances such as homo- or copolymers, e.g., polyvinyl alcohol, polyvinyl alcohol partial acetal, poly-N-vinyl pyrrolidone, polyacrylic acid, polymethacrylic acid, polyacrylamide, polyvinyl imidazole or polyvinyl pyrazole, etc.

As gelatin, not only lime processed gelatin but also acid treated gelatin and enzyme treated gelatine described in *Bull. Soc. Sci. Phot. Japan*, No. 16 page 30 (1966) may be used. Further, hydrolyzed products or enzymatic decomposition products of gelatin can be used, too. Suitable gelatin derivatives which can be used include those obtained by reacting gelatin with various compounds such as acid halides, acid anhydrides, isocyanates, bromoacetic acid, alkanesultones, vinylsulfonamides, maleinimide compounds, polyalkylene oxides or epoxy compounds, etc. Examples of these compounds are described in U.S. Pat. Nos. 2,614,928, 3,132,945, 3,186,846 and 3,312,553, British Pat. Nos. 861,414, 1,033,189 and 1,005,784, and Japanese Patent Publication No. 26845/67, etc.

As the above described gelatine-graft polymers, it is possible to use those which are prepared by grafting homo- or copolymers of vinyl monomers such as acrylic acid, methacrylic acid, derivatives thereof such as esters or amides, etc., acrylonitrile or styrene, etc. on gelatin. Particularly, it is preferred to use graft polymers composed of gelatin and polymers having a some degree of compatibility with gelatin, for example, polymers of acrylic acid, methacrylic acid, acrylamide, methacrylamide or hydroxyalkyl methacrylate, etc. Examples of such compounds are described in U.S. Pat. Nos. 2,763,625, 2,831,767 and 2,956,884, etc.

Typical synthetic high molecular weight substances are those described in, for example, German Patent Application (OLS) No. 2,312,708, U.S. Pat. Nos. 3,620,751 and 3,879,205 and Japanese Patent Publication No. 7561/68.

In order to prevent fogging in the process for producing light-sensitive materials, during storage or during photographic processings or to stabilize photographic properties, various compounds can be incorporated in the photographic emulsions in the present invention. For example, it is possible to add various compounds known as antifogging agents or stabilizers, such as thiazoles, for example, benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles and mercaptotetrazoles (particularly, 1-phenyl-5-mercaptotetrazole), etc.; mercaptopyrimidines; mercaptotriazines; thioketo compounds such as oxazolinethione; azindenes, for example, triazaindenes, tetrazaindenes (particularly, 4-hydroxyl substituted (1,3,3a,7)tetrazaindenes) and pentazaindenes, etc.; benzenethiosulfonic acid, benzenesulfinic acid or benzenesulfonamide, etc. For example, it is possible to use the compounds described in U.S. Pat. No. 3,954,474 and 3,982,947 and Japanese Patent Publication 28660/77.

The photographic emulsion layers in photographic light-sensitive materials of the present invention may contain polyalkylene oxides or derivatives thereof such as the ethers, esters or amines thereof, etc., thioether compounds, thiomorpholines, quaternary ammonium salt compounds, urethane derivatives, urea derivatives, imidazole derivatives and 3-pyrazolidones, etc. for the purpose of increasing sensitivity, improving contrast or accelerating development. For example, it is possible to use those compounds described in U.S. Pat. Nos. 2,400,532, 2,423,549, 2,716,062, 3,617,280, 3,772,021 and 3,808,003 and British Pat. No. 1,488,991, etc.

The photographic emulsions used in the present invention may be spectrally sensitized with methine dyes or other dyes. Examples of dyes which can be used include cyanine dyes, merocyanine dyes, complex cyanine dyes, complex merocyanine dyes, holopolar cyanine dyes, hemicyanine dyes, styryl dyes and hemioxonol dyes. Particularly useful dyes are cyanine dyes, merocyanine dyes and complex merocyanine dyes. In these dyes, it is possible to have any nucleus conventionally used for cyanine dyes as the basic heterocyclic nucleus. Namely, it is possible to have pyrroline nucleus, oxazoline nucleus, thiazoline nucleus, pyrrole nucleus, oxazole nucleus, thiazole nucleus, selenazole nucleus, imidazole nucleus, tetrazole nucleus and pyridine nucleus, etc.; the above described nuclei to which an alicyclic hydrocarbon ring is fused; and the above described nuclei to which an aromatic hydrocarbon ring is fused, namely, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus, etc. These nuclei may have substituents on the carbon atoms thereof.

In merocyanine dyes and complex merocyanine dyes, 5- or 6-member heterocyclic nuclei such as a pyrazolin-5-one nucleus, a thiohydantoin nucleus, a 2-thioxazolidine-2,4-dione nucleus, a thiazoline-2,4-dione nucleus, a rhodanine nucleus or a thiobarbituric acid nucleus, etc. may be present as nuclei having a ketomethylene structure.

Examples of suitable sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588 and Japanese Patent Publication Nos. 14030/69 and 24847/77.

These sensitizing dyes may be used alone, or combinations of them can be used if desired. Combinations of sensitizing dyes are used frequently for the purpose of, particularly, supersensitization. Examples of such have been described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78 and Japanese Patent Application (OPI) Nos. 110618/77 and 109925/77, etc.

The emulsions may contain dyes which do not have a spectral sensitization function themselves or substances which do not substantially absorb visible light but exhibit supersensitization together with the sensitizing dyes. For example, they may contain aminostyryl compounds (for example, those described in U.S. Pat. Nos. 2,933,390 and 3,635,721), aromatic organic acid-formaldehyde condensation products (for example, those described in U.S. Pat. No. 3,743,510), cadmium salts and azaindene compounds, etc. Combinations described in U.S. Pat. Nos. 3,615,613, 3,615,641, 3,617,295 and 3,635,721 are particularly useful.

In the light-sensitive materials produced according to the present invention, the hydrophilic colloid layers may contain water soluble dyes as filter dyes or for the purpose of anti-irradiation and for other purposes. Examples of such dyes include oxonol dyes, hemioxonol dyes, styryl dyes, merocyanine dyes, cyanine dyes and azo dyes. Of these, oxonol dyes, hemioxonol dyes and merocyanine dyes are useful. Examples of dyes which can be used include those described in British Patents 584,609 and 1,177,429, Japanese Patent publication (OPI) Nos. 85130/73, 99620/74, 11420/74 and 108115/77 and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

In the light-sensitive materials produced according to the present invention, the photographic emulsion layers and other hydrophilic colloid layers may contain whitening agents such as stilbene type, triazine type, oxazole type or coumarine type whitening agents. They may be water-soluble, and water-insoluble whitening agents may be used in the form of a dispersion.

Examples of suitable fluorescent whitening agents are described in U.S. Pat. Nos. 2,632,701, 3,169,840 and 3,359,102 and British Pat. Nos. 852,075 and 1,319,763, etc.

In practicing the present invention, the following known anti-fading agents can be used also. Further, color image stabilizers which can be used in the present invention may be used alone or as a combination of two or more of them. Examples of known anti-fading agents include hydroquinone derivatives described in U.S. Pat. Nos. 2,360,290, 2,418,613, 2,675,314, 2,701,197, 2,704,713, 2,728,659, 2,732,300, 2,735,765, 2,710,801 and 2,816,028, and British Pat. No. 1,363,921, etc., gallic acid derivatives described in U.S. Pat. Nos. 3,457,079 and 3,069,262, etc., p-alkoxyphenols described in U.S. Pat. Nos. 2,735,765 and 3,698,909 and Japanese Patent Publication Nos. 20977/74 and 6623/77, p-oxyphenol derivatives described in U.S. Pat. Nos. 3,432,300, 3,573,050, 3,574,627 and 3,764,337 and Japanese Patent Application (OPI) Nos. 35633/77, 147434/77 and 152225/77, and bisphenols described in U.S. Pat. No. 3,700,455, etc.

The light-sensitive materials produced according to the present invention may contain hydroquinone derivatives, aminophenol derivatives, gallic acid derivatives and ascorbic acid derivatives, etc. as anti-color-fogging agents. Examples of such are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93928/75, 110337/75 and 146235/77 and Japanese Patent Publication No. 23813/75.

The present invention can be employed as multilayer multicolor photographic materials having at least two layers each with a different spectral sensitivity, on a support. Multilayer natural color photographic materials generally have at least a red-sensitive silver halide emulsion layer, at least a green-sensitive silver halide emulsion layer and at least a blue-sensitive silver halide emulsion layer on a base. The order of these layers is suitably selected as needed. In general, the red-sensitive emulsion layer contains a cyan coupler, the green-sensitive emulsion layer contains a magenta coupler, and the blue-sensitive emulsion layer contains a yellow coupler, but, if desired, other combinations can be utilized.

In order to carry out photographic processing of the light-sensitive materials of the present invention, any known process can be used and known processing solutions can be used, also. Further, the processing temperature can be selected from a range of 18° C. to 50° C. in general, but a temperature lower than 18° C. or a temperature higher than 50° C. can be used, if desired. It is possible to utilize any development processing for forming silver images (black-white photographic processing) and color photographic processing comprising development for forming dye images, according to the purpose.

The color developing solution employed is generally composed of an alkaline aqueous solution containing a color developing agent. Suitable color developing agents which can be used include known primary aromatic amine developing agents, for example, phenylenediamines (for example, 4-amino-N,N-diethylaniline, 3-methyl-4-amino-N,N-diethylaniline, 4-amino-N-ethyl-N-$\beta$-hydroxyethylaniline, 3-methyl-4-amino-4-ethyl-N-$\beta$-hydroxyethylaniline, 3-methyl-4-amino-N-ethyl-N-$\beta$-methanesulfonamidoethylaniline and 4-amino-3-methyl-N-ethyl-N-$\beta$-methoxyethylaniline, etc.).

In addition, the compounds described in L.F.A. Mason, *Photographic Processing Chemistry*, pages 226–229 (published by Focal Press, 1966), U.S. Pat. Nos. 2,193,015 and 2,592,364 and Japanese Patent Application (OPI) No. 64933/73, etc. may be used.

The color developing solution may contain pH buffer agents such as alkali metal sulfites, carbonates, borates or phosphates, and development restrainers or antifogging agents such as bromides, iodides or organic antifoggants, etc. Further, the developing solution may contain, as the occasion demands, water softeners, preservatives such as hydroxylamine, organic solvents such as benzyl alcohol or diethylene glycol, development accelerators such as polyethylene glycol, quaternary ammonium salts or amines, dye forming couplers, competing couplers, fogging agents such as sodium borohydride, auxiliary developing agents such as 1-phenyl-3-pyrazolidone, viscosity increasing agents, polycarboxylic acid type chelating agents described in U.S. Pat. No. 4,083,723, and antioxidants described in German Patent Application (OLS) No. 2,622,950, etc.

The photographic emulsion layers after color development are generally subjected to bleaching processing. The bleaching processing may be carried out simultaneously with the fixing processing or may be carried out separately. Suitable bleaching agents include compounds of polyvalent metals such as iron (III), cobalt (III), chromium (VI) or copper (II), etc., peracids quinones and nitroso compounds, etc. For example, it is possible to use ferricyanides, bichromates, organic complex salts of iron (III) or cobalt (III), for example, complex salts of aminopolycarboxylic acids such as ethylenediaminetetraacetic acid, nitrilotriacetic acid or 1,3- diamino-2-propanol-tetraacetic acid, etc. or organic acids such as citric acid, tartaric acid or malic acid, etc.; persulfates, permanganates; and nitrosophenol, etc. Of these, potassium ferricyanide, sodium ethylenediaminetetraacetato iron (III) complex and ammonium ethylenediaminetetraacetato iron (III) complex are particularly useful. Ethylenediaminetetraacetato iron (III) complex salts are available in both bleaching solution and one-bath bleach-fixing solution and it is possible to add various additives such as bleaching accelerators described in U.S. Pat. Nos. 3,042,520 and 3,241,966 and Japanese Patent Publication Nos. 8506/70 and 8836/70, etc., thiol compounds described in Japanese Patent Application (OPI) No. 65732/78, and other compounds.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material containing at least one coupler having a ballast group represented by the following general formula (I):

(I)

wherein

represents a substituted or unsubstituted aromatic heterocyclic ring, and m represents an integer of 1 or 2.

2. The light-sensitive material of claim 1, wherein said ballast group is represented by the following general formula (II)

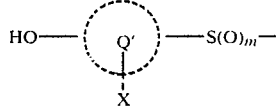
(II)

wherein

represents an unsubstituted aromatic heterocyclic ring containing at least one of an oxygen atom and a sulfur atom and wherein X represents a hydrogen atom, a halogen atom, an alkyl group, an aryl group, a heterocyclic group, a hydroxy group, an alkoxy group, an aryloxy group, an acylamino group, a sulfonamido group, a carbamoyl group, a sulfamoyl group, a ureido group, an alkoxycarbonyl group, an alkoxycarbonylamino group, a sulfonyl group, an alkylthio group, a cyano group, a nitro group or a carboxyl group and m represents an integer of 1 or 2.

3. The light-sensitive material of claim 2, wherein said coupler is represented by the following general formula (III).

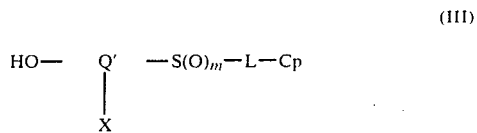
(III)

wherein Cp represents a coupler residue, L represents a bond or a divalent linking group and X and m each have the same meaning as in the general formula (II) of claim 2.

4. The light-sensitive material of claim 3, wherein Cp represents a cyan coupler residue, a magenta coupler residue or a yellow coupler residue.

5. The light-sensitive material of claim 3, wherein Cp represents a coupler residue for forming a black dye, a grey dye or a coloring compound.

6. The light-sensitive material of claim 3, wherein L represents

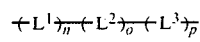

wherein n, o and p represent each 0 or an integer of 1, $L^1$ represents a divalent group selected from the group consisting of groups of the formula

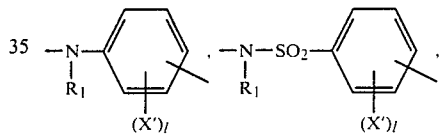

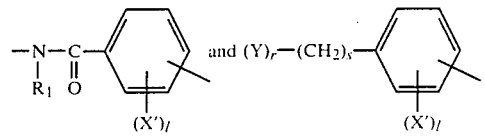

$L^2$ represents a divalent group selected from groups of the formula

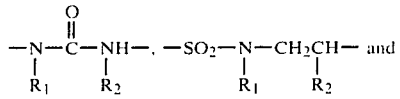

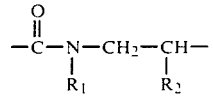

and $L^3$ represents a divalent group selected from groups of the formula

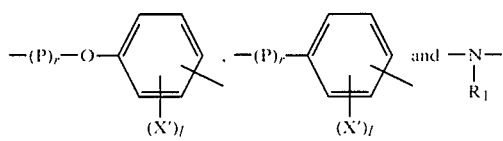

wherein $R_1$ and $R_2$ represent each a hydrogen atom, an alkyl group having 1 to 20 carbon atoms or an aryl group having 6 to 20 carbon atoms, X' has the same meaning as described in claim 2 for X or a hydrogen atom; Y represents —O— or —S—; P represents

or —$SO_2$—; r represents 0 or an integer of 1; s represents 0 or an integer of 10; and l is an integer of 1 to 4.

7. The light-sensitive material of claim 2, wherein Cp represents

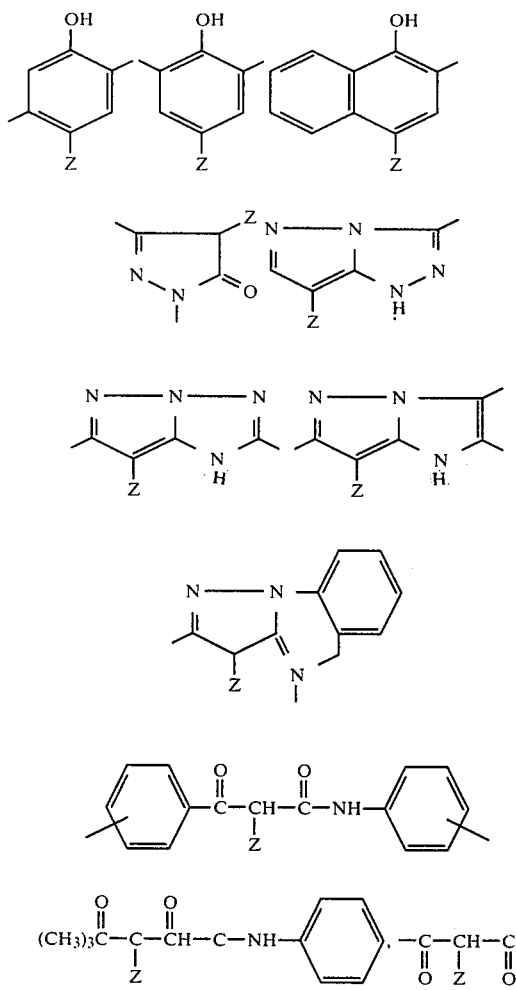

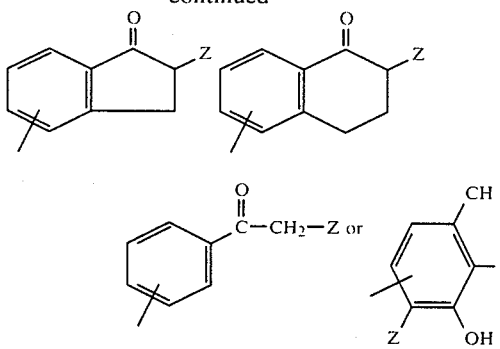

wherein Z represents a hydrogen atom or an atom or group which is released upon coupling with an oxidation product of a color developing agent.

8. The light-sensitive material of claim 2, wherein

Q' is selected from groups of formula

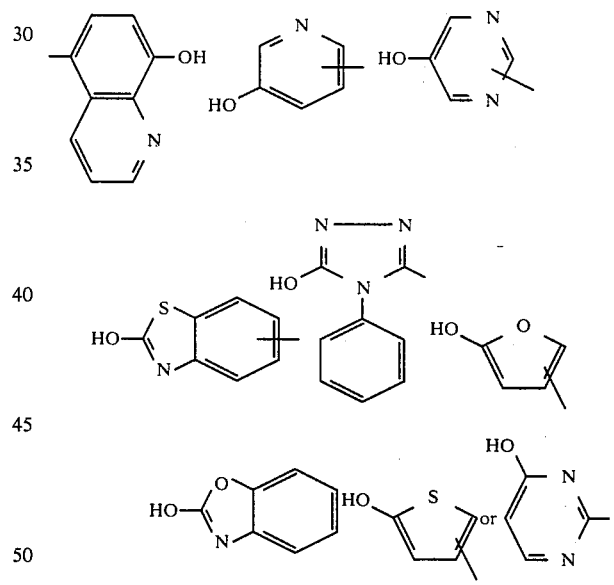

9. The light-sensitive material of claim 1, wherein said coupler is present in an amount of $2 \times 10^{-3}$ to $5 \times 10^{-1}$ moles of coupler per mole of silver in the silver halide emulsion layer.

* * * * *